United States Patent
Matsutani et al.

(10) Patent No.: US 6,183,484 B1
(45) Date of Patent: Feb. 6, 2001

(54) SUTURE LIGATING DEVICE

(75) Inventors: Kanji Matsutani; Takayuki Matsumoto, both of Takanezawa-machi (JP)

(73) Assignee: Mani, Inc., Tochiga (JP)

( * ) Notice: Under 35 U.S.C. 154(b), the term of this patent shall be extended for 0 days.

(21) Appl. No.: 09/379,387

(22) Filed: Aug. 23, 1999

(51) Int. Cl.[7] .................................................. A61B 17/00
(52) U.S. Cl. ............................................ 606/144; 606/148
(58) Field of Search ................................... 606/144, 148, 606/205, 206, 207, 139, 145

(56) References Cited

U.S. PATENT DOCUMENTS

| | | | |
|---|---|---|---|
| Re. 14,923 | * | 7/1920 | Smit ...................................... 606/144 |
| 2,286,578 | * | 6/1942 | Sauter ................................... 606/144 |
| 5,254,126 | * | 10/1993 | Filipi et al. ........................... 606/146 |
| 5,522,820 | * | 6/1996 | Caspari et al. ........................ 606/148 |
| 5,690,652 | * | 11/1997 | Wurster et al. ....................... 606/144 |
| 5,797,927 | * | 8/1998 | Yoon .................................... 606/144 |
| 5,843,099 | * | 11/1999 | Nichols et al. ........................ 606/144 |
| 5,980,538 | * | 11/1999 | Fuchs et al. ........................... 606/145 |

FOREIGN PATENT DOCUMENTS

| | | |
|---|---|---|
| 5-317321 | 12/1993 | (JP) . |
| 9-56719 | 3/1997 | (JP) . |

* cited by examiner

Primary Examiner—Gary Jackson

(57) ABSTRACT

A suture ligating device used in a endoscopic surgery which can reliably transfer a knot of a suture formed outside a human body to inner tissues to be ligated inside the human body without causing a separation of the knot from the suture ligating device. The suture ligating device includes a manipulation portion, first and second rod members provided at the manipulation portion and making a relative movement in response to an operation of the manipulation portion, first and second top end members provided at an end of the first rod member, concaves formed at the ends of the first and second top end members, and the third top end member provided at an end of the second rod member to perform an open and close movement in response to the relative movement of the first and second rod members.

20 Claims, 16 Drawing Sheets

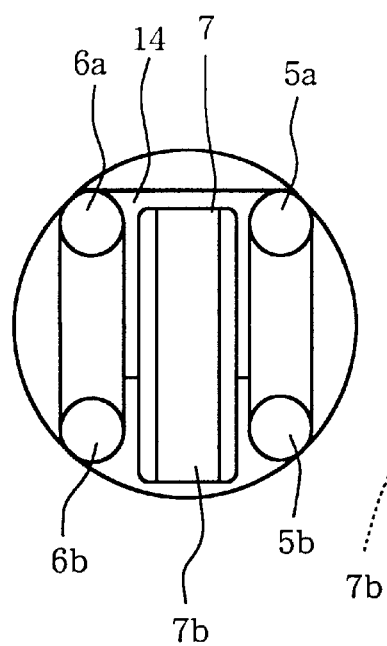
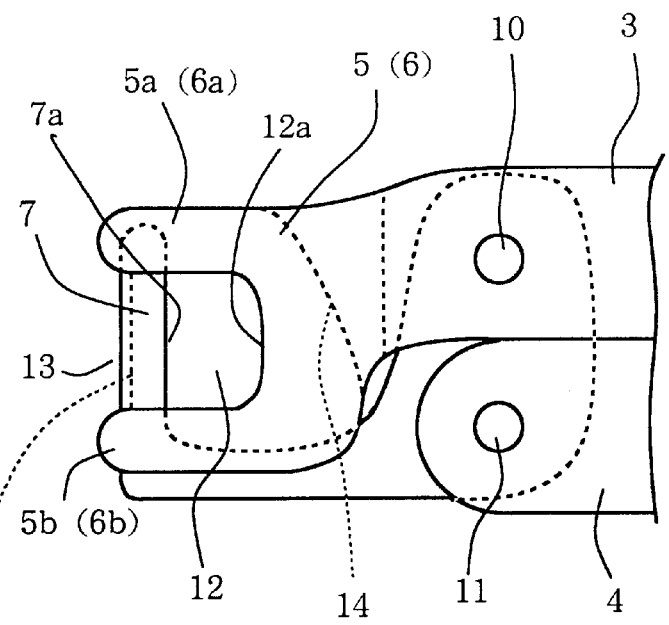
Fig2b  Fig2a
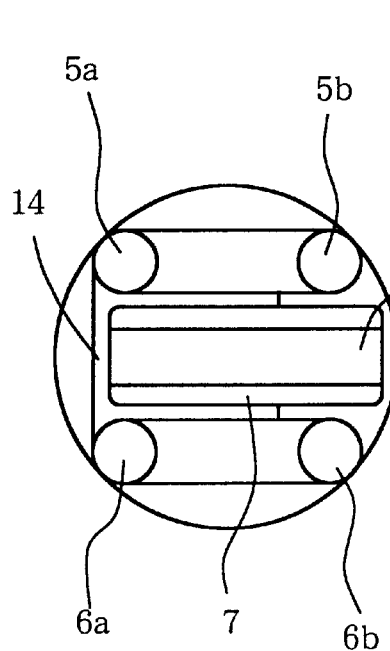
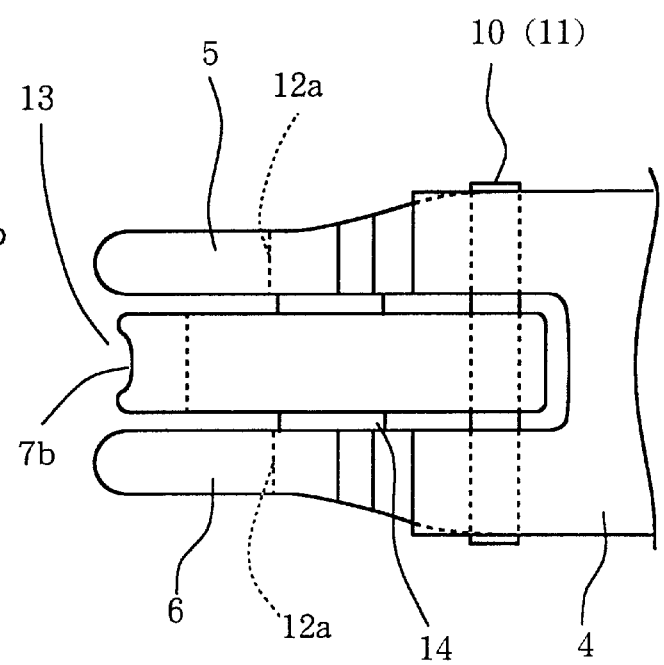
Fig3b  Fig3a

SUTURE LIGATING DEVICE

FIELD OF THE INVENTION

This invention generally relates to a suture technology for ligating tissues at a small area within a human body to be used in performing endoscopic surgery, and more particularly, to a suture ligating device for sending a knot of a suture formed outside the human body to an intended location in the human body to ligate the tissues therein.

BACKGROUND OF THE INVENTION

Recently, surgery using an endoscope (endoscopic surgery) is getting more widely performed. While the conventional surgery methods need to largely dissect the abdomen or chest of a human body for cutting, suturing or ligating the tissues to be treated, an endoscopic surgery only needs to cut a hole of a minimum size in the abdomen or other regions. Due to the smallness of the cut, early recovery of the patient is possible.

Endoscopic surgery is performed as follows. First, a trocar having a reverse stop valve is inserted into the hole cut in an abdomen. A gas is charged therethrough into the abdominal cavity to create a space at the surgery region. Thereafter, surgery is performed by inserting scalpels, forceps and the like in the abdominal cavity through the hollow space of the trocar. In order to monitor the surgery, another hole is created in the abdomen to insert another trocar to provide a monitoring camera therein for monitoring the operation of the surgery.

Since the space of the abdominal cavity is limited, surgeons must insert slender devices in a narrow space by monitoring the display to perform the surgery appropriately. Depending on the circumstances, surgeons must suture the tissue of the dissected portion or ligate a number of blood vessels.

The above suturing procedure is performed as follows. A guide device for guiding a needle having a suture, formed for example in a forceps shape, such as a guide device disclosed in Japanese Laid Open Patent Publication No. 9-56719, is inserted through the space in the trocar. Then, the tissues to be sutured are grasped and pierced by the needle having a suture. Thereafter, both ends of the piercing suture is pulled back outside the human body through the space of the trocar. Subsequently, a tie or knot (hereinafter referred to as a "knot") of the suture is formed outside the human body. This knot is then sent back to the place where the tissues are ligated by using a suture sending device called a "knot pusher", an example of which is disclosed in Japanese Laid Open Patent Publication No. 5-317321. Then, the tissues are ligated at that place. By repeating this operation more than two times, a ligation which will not get loose, such as called a "surgeon's knot", can be achieved.

However, at the time the knot is sent to the inner cavity with use of the knot pusher through the space of the trocar, the movement of the knot pusher is hindered by the reverse stop valves as well as the narrow space of the tube of the trocar, hitting many spots inside the trocar. Owing to this problem, the knot of the suture is sometimes separated from the knot pusher. If the knot has already passed the trocar and is reached the space of the abdominal cavity, it is still possible to recapture the knot by the knot pusher through monitoring the knot by the camera display. However, such an operation for recapturing the knot takes a long time. If the knot is separated from the knot pusher inside the trocar, it is extremely difficult to recapture the knot. Thus, the knot pressing operating has to start over again, taking a much longer time.

In addition, as described above, since the number of the knots to be tied for each tissue ligating is at least two, possibility of occurrence of the above trouble exists at least two times at one place. This results in a heavy burden to surgeons as well as patient. Further, the knot ligated by the first operation sometimes becomes loose before the second knot is sent thereto, resulting in the failure of sufficiently joining the tissues.

SUMMARY OF THE INVENTION

Therefore, it is an object of the present invention to provide a suture ligating device which can reliably send a knot or knots of the suture tied outside the human body to the tissues to be ligated inside the human body without causing a separation of the knot from the device.

It is another object of the present invention to provide a suture ligating device which can transfer two knots at the same time to the tissues to be ligated inside the human body and tighten the knots.

It is a further object of the present invention to provide a suture ligating device which can smoothly transfer one or more knots formed outside of the human body to the tissues to be ligated inside the human body without causing friction between the suture and the ligating device.

It is a further object of the present invention to provide a suture ligating device which can securely transfer one or more knots to the tissues to be ligated by forming a closed space in which at least one knot is confined.

It is a further object of the present invention to provide a suture ligating device which can easily tighten the knots for the tissues to be ligated by widening a top end portion of the suture ligating device.

The above object of the present invention is achieved by providing a suture ligating device which includes a manipulation portion, a first and second rod members for making a relative movement to each other by an operation of the manipulation portion, first and second top end members provided at the top ends of the first and second rod members, and a third top end member connected to the second rod member for entering in a space provided between the first and second top end members in accordance with the relative movement of the first and second rod members, wherein the first and second top end members are provided with concaves opening in the top end direction, each of the concaves is separated from, each other by a predetermined distance, and the third top end member enters into a position located at the top end side over a bottom of the concaves of the first and second top end members.

The first and second rod members of the above device are provided in parallel and the relative movement of these members are made in the longitudinal direction of these slender members. At the time the third top end member enters into the space between the first and second top end members, the top end of the protrusions forming the concavity of the first and second top end members may protrude beyond the third top end member so that the second concavity is formed by the third top end member and the protrusions of the first and second top end members.

In a further aspect of the present invention, the third top end member may be provided with a projection at its top end side such that the projection and a protrusion of the first and second top end member protruding beyond the third top end member may form the second concavity. Further, the top end face of the third top end member may be formed in a concave shape so that the knot of the suture placed in the second concavity is prevented from directly contacting with the top end face of the third top end member. Further, a part of the first and the second top end members may be integrally connected by a connecting member.

In a further aspect of the present invention, the suture ligating device is structured so that all of first, second and third top end members perform open and close movement in response to an operation of a manipulation portion of the suture ligating device. The suture ligating device includes a manipulation portion, first and second slender members for making a relative movement to each other by manipulating the manipulation portion, first and second top end members provided at the top end of the first and second slender members, and a third top end member connected with the second slender member and moving between the first and second top end members in accordance with the relative movement of the first and second slender member, wherein the first and second top end members are provided with concavities opening in the top end direction, the first and second top end members are separated to each other by a predetermined distance which can be changed, and the third top end member enters into a space located at the top end side of the bottom of the concavities of the first and second top end members.

The first and second top end members are provided with a link mechanism by which the distance between the first and second top end members can be changed. The link mechanism is actuated by the relative movement of the first and second slender members in response to the operation of the manipulation portion. The distance between the first and second top end members is varied only when the relative movement of the first and second slender members exceeds a predetermined degree. In contrast, the third top end member is moved immediately by the relative movement of the first and second slender members.

In the suture ligating device of the present invention, the first and second top end members and the third top end member form a closed space when the third top end member enters in the space between the first and second top end members. Accordingly, a knot of a suture formed outside of a human body is secured in the closed space and transferred to tissues to be ligated inside of the human body.

Further in the suture ligating device, the first and second top end members and the third top end member form a closed space when the third top end member enters in the space formed between the first and second top end members. First and second knots of a suture are formed outside of a human body, and accordingly, the first knot is placed on an end surface formed by the first, second and third top end members, and the second knot is secured in the closed space, wherein the first and second knots are transferred to tissues to be ligated inside of the human body by inserting the suture ligating device in the human body while applying an appropriate pulling tension to the suture.

Consequently, a knot or knots can be transferred to the inner body of the patient without being lost or separated from suture ligating device, and thus the tissues are reliably and efficiently ligated therein.

BRIEF EXPLANATION OF THE DRAWINGS

FIG. 2(a) is a side view of the top end portion of the suture ligating device of FIG. 1, and FIG. 2(b) is a front view of the top end portion of the suture ligating device of FIG. 1.

FIG. 3(a) is a plan view of the top end portion of the suture ligating device of FIG. 1, and FIG. 3(b) is a front view of the top end portion of the suture ligating device of FIG. 1.

DETAILED DESCRIPTION OF THE PREFERRED EMBODIMENT

Referring now the drawings, the preferred embodiments of the present invention will be described in detail.

Figures 1A, 1B, 1C, 1D:
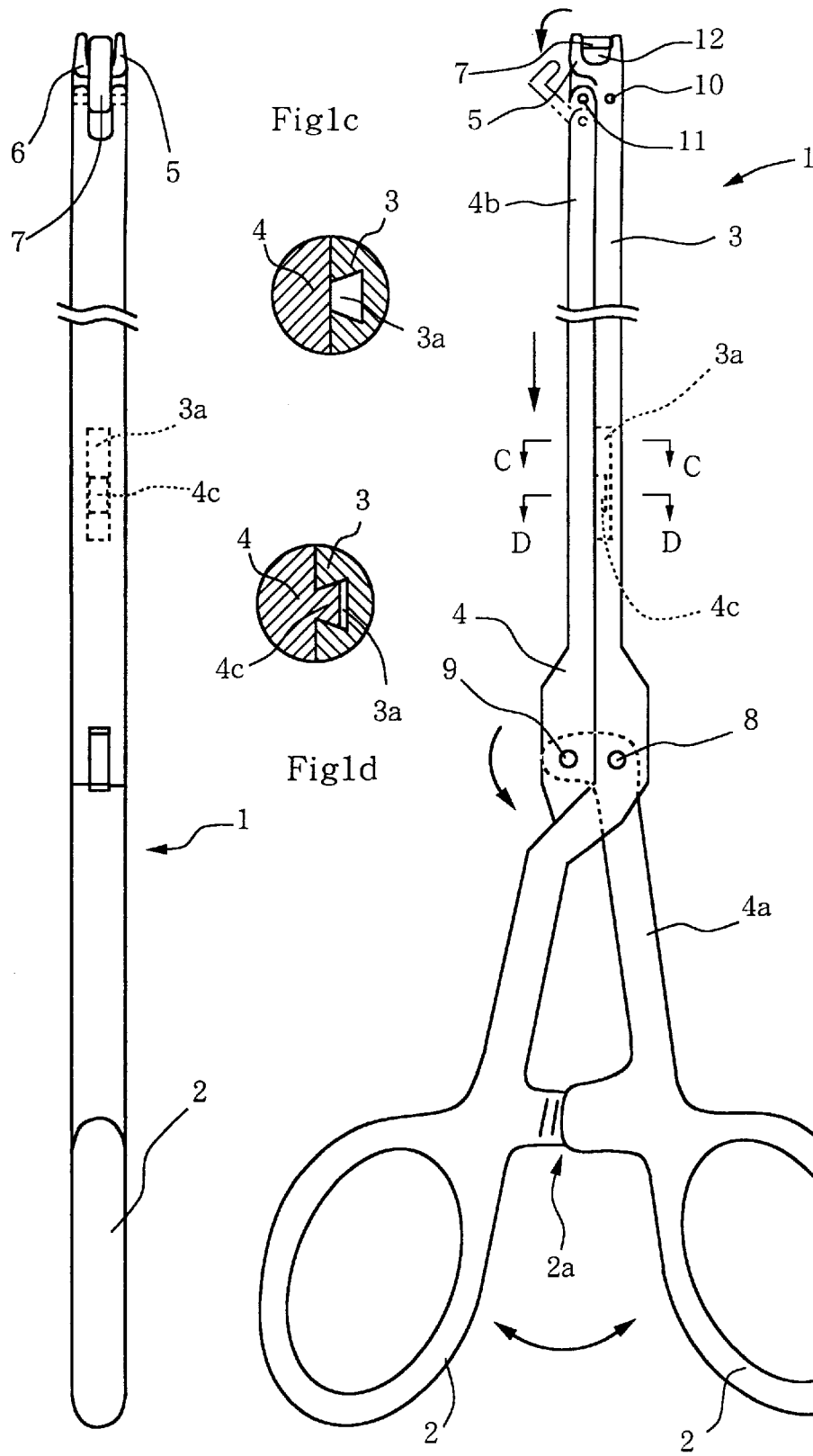
FIG. 1(a) is a side view of the suture ligating device in accordance with a first embodiment of the present invention.
FIG. 1(b) is a plan view of the suture ligating device in the first embodiment.
FIG. 1(c) is an enlarged cross sectional view taken along the line C—C of FIG. 1(b)
FIG. 1(d) is an enlarged cross sectional view taken along the line D—D of FIG. 1(b).
Figure 4:
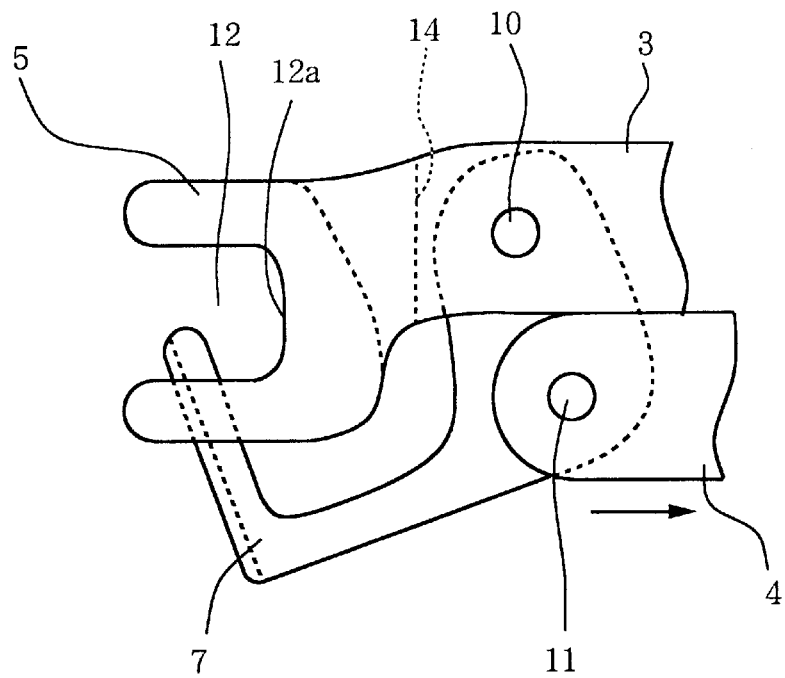
FIG. 4 is a side view of the top end portion of the suture ligating device of FIG. 1 showing the state wherein the third top end member is opened.

FIG. 1 shows an overall structure of the suture ligating device in the first embodiment of the present invention. FIG. 1(a) is a side view, FIG. 1(b) is a plan view, FIG. 1(c) is an enlarged sectional view taken along the line C—C of FIG. 1(b), and FIG. 1(d) is an enlarged sectional view taken along the line D—D of FIG. 1(b). FIGS. 2, 3 and 4 respectively show expanded views of the top end portion of the suture ligating device 1.

As shown in these drawings, the suture ligating device 1 of the present invention is comprised of manipulation portions 2 formed in a circle shape similar to a grip of scissors, first and second rod members 3 and 4 extending from the manipulation portions 2, first and second top end members 5 and 6 each having a plate shape formed at an end of the first rod member 3, and a third top end member 7 connected to an end of the second rod member 4 and moved between the first and second top end members 5 and 6.

The manipulation portion 2 is provided with a stopper mechanism 2a comprised of a protrusion formed on one of the manipulation portions and grooves of a saw tooth shape formed on the other manipulation portion. By fitting the protrusion with the grooves, the manipulation portions 2 can keep its closed state. However, the stopper mechanism 2a is not an essential element, and the suture ligating device 1 of the present invention can achieve its object without having the stopper mechanism 2a.

In the example of FIGS. 1–4, while the first rod member 3 is formed integrally with one of the manipulation portions 2, the second rod member 4 is divided into a unit 4a in the side of the manipulation portion and a unit 4b in the top end side. The top end of the unit 4a in the manipulation portion side is bent about 90° as shown by the dotted line of FIG. 1(b). Axes 8 and 9 are provided at the corner and the top end of the bent portion, respectively. The axis 8 rotatably connects the unit 4a of the manipulation portion and the first rod member 3. The axis 9 rotatably connects the units 4a in the manipulation side and the unit 4b in the top end side.

A dovetail groove 3a is provided at the straight portion of the first rod member 3. A protrusion 4c is provided on the second rod member 4 to fit into the dovetail groove 3a. By having this arrangement, the first and second rod members 3 and 4 are slidably connected in the longitudinal direction. This relationship is shown in the cross sectional views of FIGS. 1(c) and 1(d).

Under the foregoing configuration, by open and close movement of the manipulation portions 2, the top end of the unit 4a connected to the second rod member 4 rotates around the axis 8, which causes the forward and backward movements of the second rod member 4 in parallel with the first rod member 3. Namely, in FIG. 1, the second rod member 4 moves downward relative to the first rod member 3 when the manipulation portions 2 are opened, and moves upward when the manipulation portions 2 are closed.

As described above, the end of the first rod member 3 is provided with the first top end member 5 and the second top end member 6 which are separated from one another as shown in FIG. 1(a). Further, as shown in FIGS. 2 and 3, protrusions 5a and 5b are formed on the first top end member 5, and protrusions 6a and 6b are formed on the second top end member 6. Further in FIG. 2(a), between the protrusions 5a and 5b and between 6a and 6b, concaves 12 are formed. The top end members 5 and 6 are connected to each other at their base end by a connecting member 14. The connecting member 14 is employed for increasing the mechanical strength of each of the top end members 5 and 6, but may not be necessary when, for instance, the strength of the top end member 5 and 6 is high enough.

In this example, the third top end member 7 is formed in a U-shape as shown in FIG. 2(a), an end of which has a plate like shape. Two axes 10 and 11 are provided at the base end of the third top member 7. The axis 10 rotatably connects the third top end member 7 to the first rod member 3. The axis 11 rotatably connects the third top end member 7 to the end of the second rod member 4.

Under the configuration noted above, when the manipulation portions 2 are opened, the second rod member 4 is moved downward in FIG. 1, i.e., backward on a longitudinal axis, relative to the first rod member 3. Accordingly, the third top end member 7 rotates about the axis 10 thereby retreating from the space between the first and second top end members 3 and 4 as shown in FIG. 4, thereby creating an open space formed by the concaves 12.

A top end surface 7b of the third top end member 7 is formed in a groove like shape as best shown in FIG. 3(a). The protrusions 5a, 5b and 6a, 6b of the first and second top end members 3 and 4 extend beyond the top end surface 7b, thereby forming a second concave 13 at the end of the third top end member 7. Preferably, these concaves should be chamfered and surface treated, such as an abrasion or other polishing, so that the suture may smoothly slide on the surface of the concaves.

In the above embodiment, although the second rod member 4 is formed of the two rod like units 4a and 4b, the unit 4b at the top end side may be formed of a wire and the third top end member 7 may be provided with a spring which biases the top end member 7 toward the space between the first and second top end members 5 and 6. Furthermore, the first rod member 3 may be formed as a tubular body through which the second rod member 4 is slidably provided.

With reference to FIGS. 5–8, the method of using the suture ligating device of the present invention is explained in the following for an example of suturing the dissected tissues A1 and A2.

Figure 5:
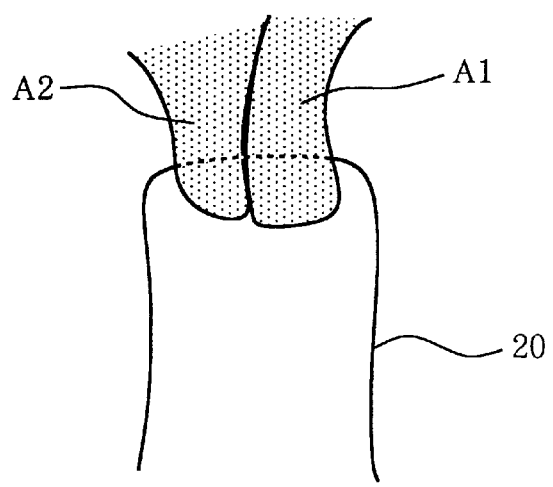
FIG. 5 is a schematic diagram showing a situation where tissues to be ligated are pierced by a suture.

As shown in FIG. 5, the tissues A1 and A2 to be sutured are aligned and pierced by the suture 20. This operation is performed with use of a guide device in a forceps shape having a thread for medical treatment such as a suture needle guide device disclosed in the Japanese Laid Open Patent Publication No. 9-56719. The ends of the suture 20 piercing through the tissues A1 and A2 are pulled back from the human body through the trocar together with the guide device.

Figure 6:
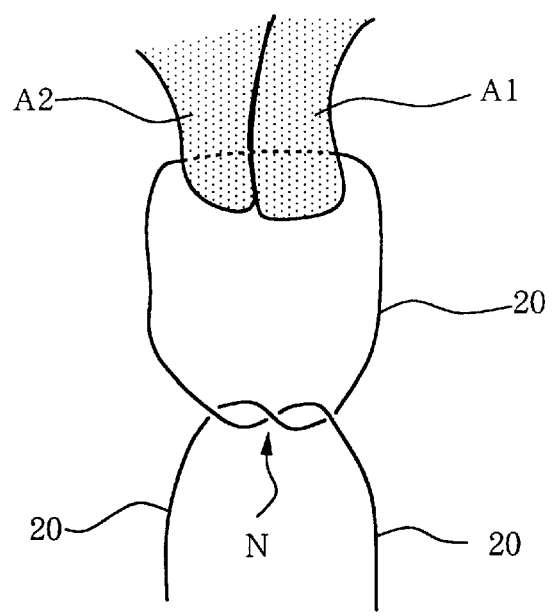
FIG. 6 is a schematic diagram showing a situation where a knot is formed.

Thereafter, a knot N is formed on the suture 20 which is pulled back from the human body to outside as shown in FIG. 6. Then, by retreating the third top end member 7 from the space between the first and second top end members 5 and 6 as shown in FIG. 4, the knot N is placed into the concaves of the first and second top end members 5 and 6. Thereafter, the third top end member 7 is entered into the space between the first and second top end members 5 and 6.

Figure 7:
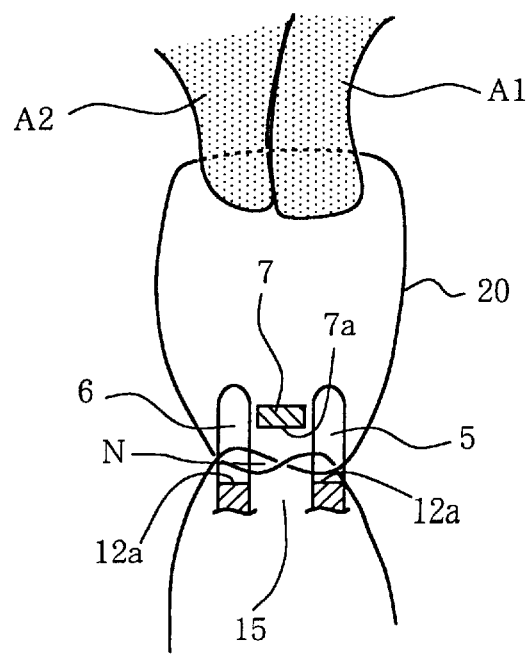
FIG. 7 is a diagram showing a situation where a knot is captured by the top end portion of the suture ligating device of the present invention.

In this manner, the knot N is confined in a closed space formed by the first and second top end members 5 and 6 and the third top end member 7 as shown in FIG. 7. Consequently, the knot N is securely captured in the closed space noted above and the third top end member 7 is inserted in the loop of the suture between the tissues A1, A2 and the knot N. Therefore, unlike the conventional method, during the course of sending the knot to the ligating place, the knot will not be lost or separated from the device.

Figure 8:
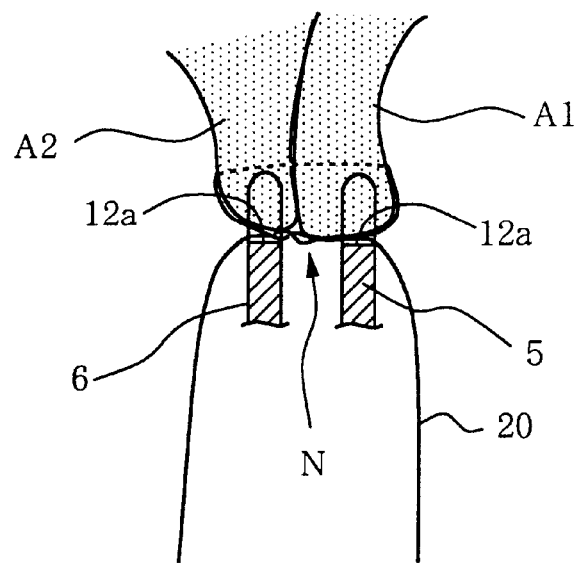
FIG. 8 is a diagram showing a situation where a knot is sent to the ligating portion and tightened therein.

Under this condition, the suture ligating device 1 is pressed toward the tissues A1 and A2, while applying an appropriate level of tension to the suture. In this event, since the knot N is not directly pressed, but rather advances by itself toward the tissues A1 and A2 by the tension applied to the suture, the knot N can be smoothly transferred to the position of the tissues A1 and A2. When reaching the tissues, the third top end member 7 is withdrawn as shown in FIG. 8. By pressing the suture ligating device further toward the tissues and applying an appropriate amount of tension to the suture, the knot N can be tightened therein. In order to form a plurality of knots, the above described operation may be repeatedly conducted by predetermined times.

Referring back to FIG. 7, the positional relationship between an inside surface 7a of the third top end member 7 and a bottom surface 12a of the concave 12 is described. At the time the third top end member 7 enters the space 15 between the first and second top end members 5 and 6, the inside surface 7a of the third top end member 7 is positioned ahead of the bottom surface 12a of the concave 12. Under this configuration, at the time of pressing the knot toward the inner tissues, the knot N held between the first and second top end members 5 and 6 can contact only with the bottom surface. Although the suture 20 and knot N look large in size in FIG. 7, an actual suture and knot are much smaller and can be completely stored within the space between the top end members 5 and 6. Therefore, the knot is smoothly transferred to the ligating location without contacting with the inside surface 7a.

Figure 9:
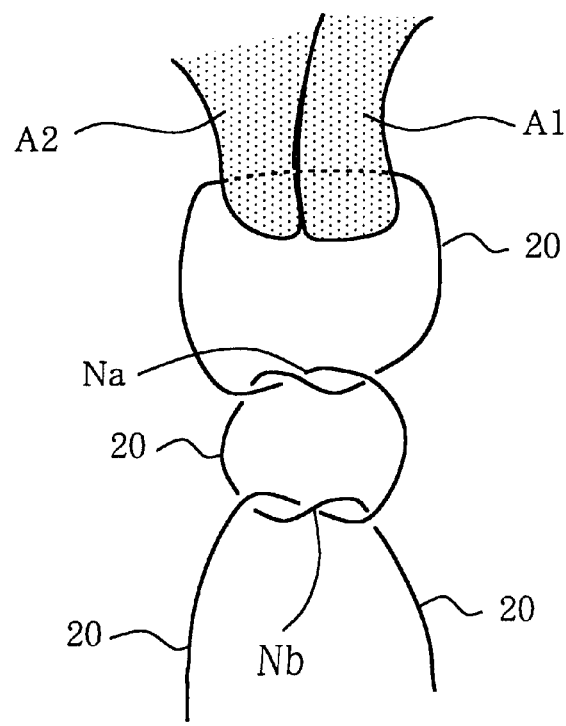
FIG. 9 is a diagram showing a situation where two knots are formed.
Figure 10:
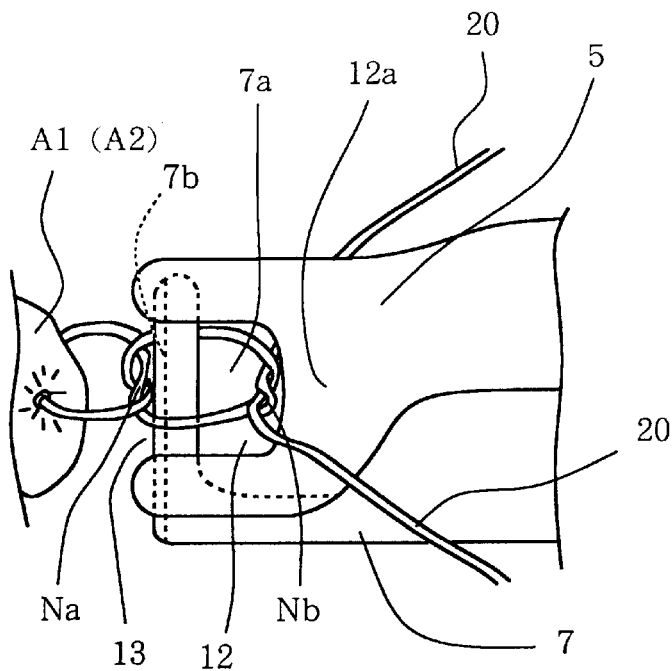
FIG. 10 is a perspective view of the top end portion of the suture ligating device of the present invention wherein the suture having two knots are captured by the top end portion of the suture ligating device of the present invention.

The suture ligating device 1 of the present invention can send two knots at a time to inner tissues of the human body for ligating the tissues therein. An example of process for sending two knots at a time is described in FIGS. 9 and 10. As shown in FIG. 5, the suture 20 piercing through the tissues is pulled back to the outside the human body where two knots Na and Nb are formed in a manner shown in FIG. 9 The third top end member 7 is retreated from the space between the first and second top end members 5 and 6. Then, the knot Nb is placed in the concave 12 of the first and second top end members 5 and 6. Thereafter, as shown in FIG. 10, the third top end member 7 enters the space between the first and second top end members 5 and 6 such that it also enters a circle formed between the knot Na and knot Nb.

By this operation, the knot Nb is secured in the closed space formed by the concave 12 of the first and second top end members 5 and 6 and the third top end member 7. The knot Na is placed at the outside of the third top end member 7. As shown in FIGS. 2 and 3, since the protrusions 5a, 5b and 6a, 6b are extending beyond the third top end member 7, the second concave 13 is formed at the outside of the third top end member 7. Thus, the knot Na is positioned on the second concave 13.

Subsequently, the suture ligating device 1 is inserted in the human body toward the tissues A1 and A2 while applying an appropriate level of tension to the suture 20. In this event, since the top end surface 7b of the third top end member 7 is formed in a concave shape, a contact area between the knot Na and the third top end member 7 is small, resulting in a small friction therebetween. Thus, the suture ligating device can smoothly transfer the knots Na and Nb toward the inner tissues.

When the knot Na positioned in the second concave 13 reaches the tissues, the knot Na is ligated therein by increasing the tension applied to the suture 20. Then, the third top end member 7 is retreated from the space between first and second the top end members 5 and 6, leaving the knot Nb. Thereafter, the tension is continuously applied to the suture 20 in that state and the device is further pressed toward the tissues to tighten the second knot therein. Consequently, two knots are transferred to the tissues and fasten the tissues by a single operation of the suture ligating device of the present invention. The ligation is made sufficiently firmly so that it will not loosen, since, unlike the conventional devices, the suture ligating device of the present invention does not need to send the second knot before the first knot becomes loose.

Figures 11A, 11B:
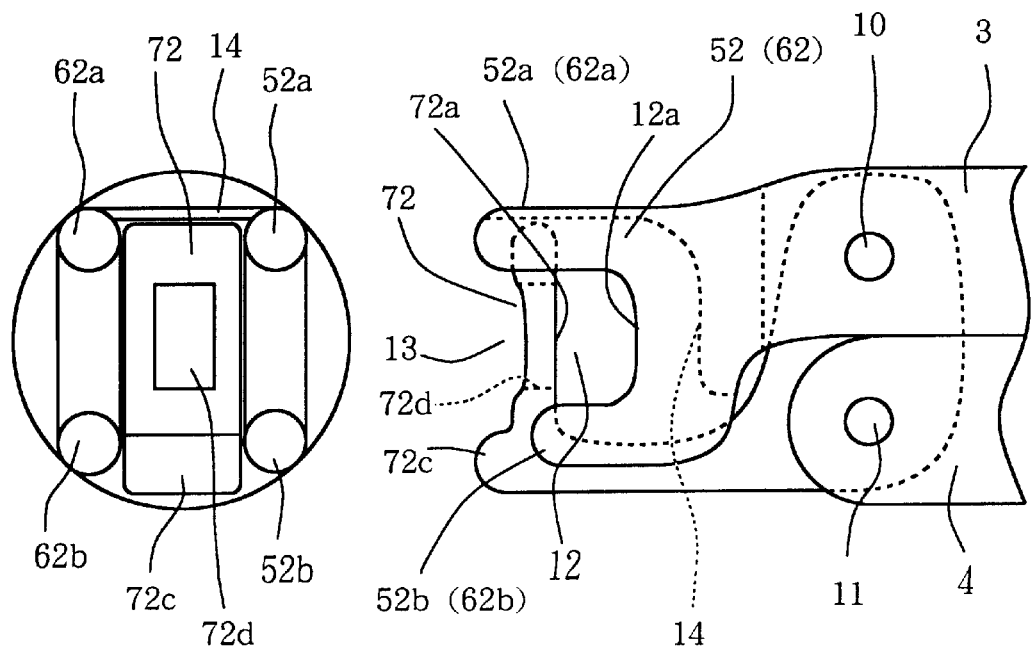
FIG. 11(a) is a side view of the top end portion of the suture ligating device according to a second embodiment of the present invention.
FIG. 11(b) is a front view of the top end portion of the suture ligating device in the second embodiment of the present invention.

FIG. 11 shows the second embodiment of the present invention. In this example, the protrusions provided at the end of the first and second top end members 5 and 6 have different height (length) from the other. In FIG. 11, thus protrusion 52b is shorter (lower) than the protrusion 52a, and protrusion 62b is shorter (lower) than the protrusion 62a. However, the third top end member 72 has a projection 72c as shown in FIG. 11(*a*) which has the same height of the longer (higher) protrusions 52a and 62a when inserted in the concave 12.

An opposing portion of the connecting member 14 against the third top end member 72 is extended toward the end of the first and second top end member 52a and 62a as shown by the dotted line, thereby increasing the mechanical strength of the first and second top end member 52 and 62. As described above, the size or connecting range of the connecting member 14 is not essential and can be varied so long as the knot will not directly contact with the connecting member and can enter the space of the concave 12 and also the third top end member 72 is able to enter the space between the first and second top end members 5 and 6.

Because of the above described configuration, after the knot Na is ligated, the third top end member 72 can be smoothly retreated from the concave 12 without having the knot Na trapped between the protrusions 52b and 62b and the third top end member 72. In this embodiment, the third top end member 72 is provided with a rectangular through hole 72d in stead of the groove. By this arrangement, in a case where a knot needs to be retracted for some reason, the knot is prevented from directly contacting with the inside surface 72a so that the knot can be smoothly retracted.

Further, the end face of the third top end member 72 is curved as a whole because of the projection 72c. By this arrangement, the second concave 13 is formed deeper so that the suture can be prevented from separating from the suture ligating device. Also, in a case where the protrusions 52a and 62a may hinder an operation for tying the knot, the protrusions 52a and 62a can be lowered to the extent of the curve of the third top end member 72.

Figures 12A, 12B:
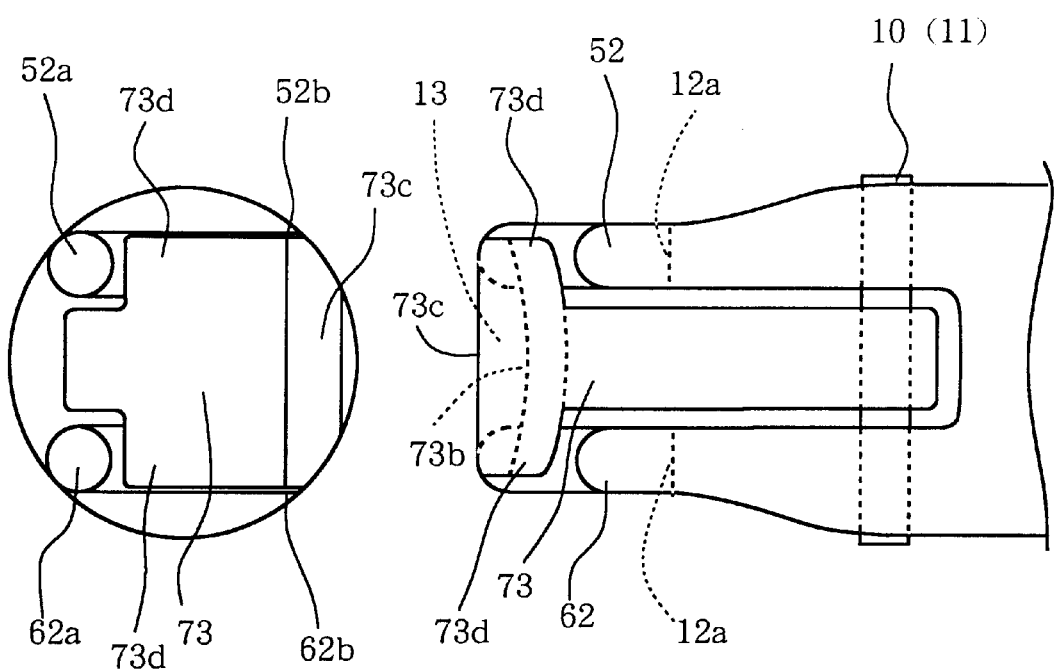
FIG. 12(a) is a side view of the top end portion of the suture ligating device in a third embodiment of the present invention.
FIG. 12(b) is a front view of the top end portion of the suture ligating device in the third embodiment of the present invention.

FIG. 12 shows the third embodiment of the present invention. FIG. 12(*a*) is a plan view and FIG. 12(*b*) is a front view of the end portion of the third embodiment. The feature of this embodiment is that the third top end member 72 has a shape different from that of FIG. 11. The projection 73c of the third top end member 73 and the first and second projections 52a and 62a are arranged in the same length (height) while an intermediate area 73b is curved inwardly to form the second concave 13 therebetween. Further, extended portions 73*d* are provided at the end of the third top end member 73 in such a way to cover the lower protrusions 52*b* and 62*b*. Thus, as shown in FIG. 12(*a*), the curved (intermediate) area 73*b* is formed between the extended portions 73*d*.

By this arrangement, the curved area 73*b* has a broader area because of the extended portions 73*d*, which makes the angle of the crossing suture at the knot close to 180 degrees. Therefore, the knot Na at the ligating location can be tightened easily and securely when the tension is provided to both ends of the suture. Further, by forming the end portion of the third top end member 73 in a curved shape, the depth and the surface area of the second concave 13 are increased, and consequently, the knot Na is securely transferred to the ligating location without separating from the suture ligating device.

In the foregoing embodiments, the shape of the manipulation portion does not need to be a forceps shape but can be other shapes such as a gun shape. Further, although the manipulation portion of this embodiment is formed to be grasped by hand, such a grasping portion may be provided separately from the manipulation portion. Thus, in such an example, the suture ligating device can be manipulated by the manipulation portion while holding the device by the separately provided grasping portion.

FIGS. 13–21 show the fourth embodiment of the present invention. In this example, first and second top end members are independent from one another and a distance therebetween can be continuously varied. In FIGS. 13–21, it should be noted that, in order to facilitate better understanding of the present invention, some lines are omitted or added, and imaginary lines are drawn, and relative sizes and shapes of some components are exaggerated.

Figure 13:
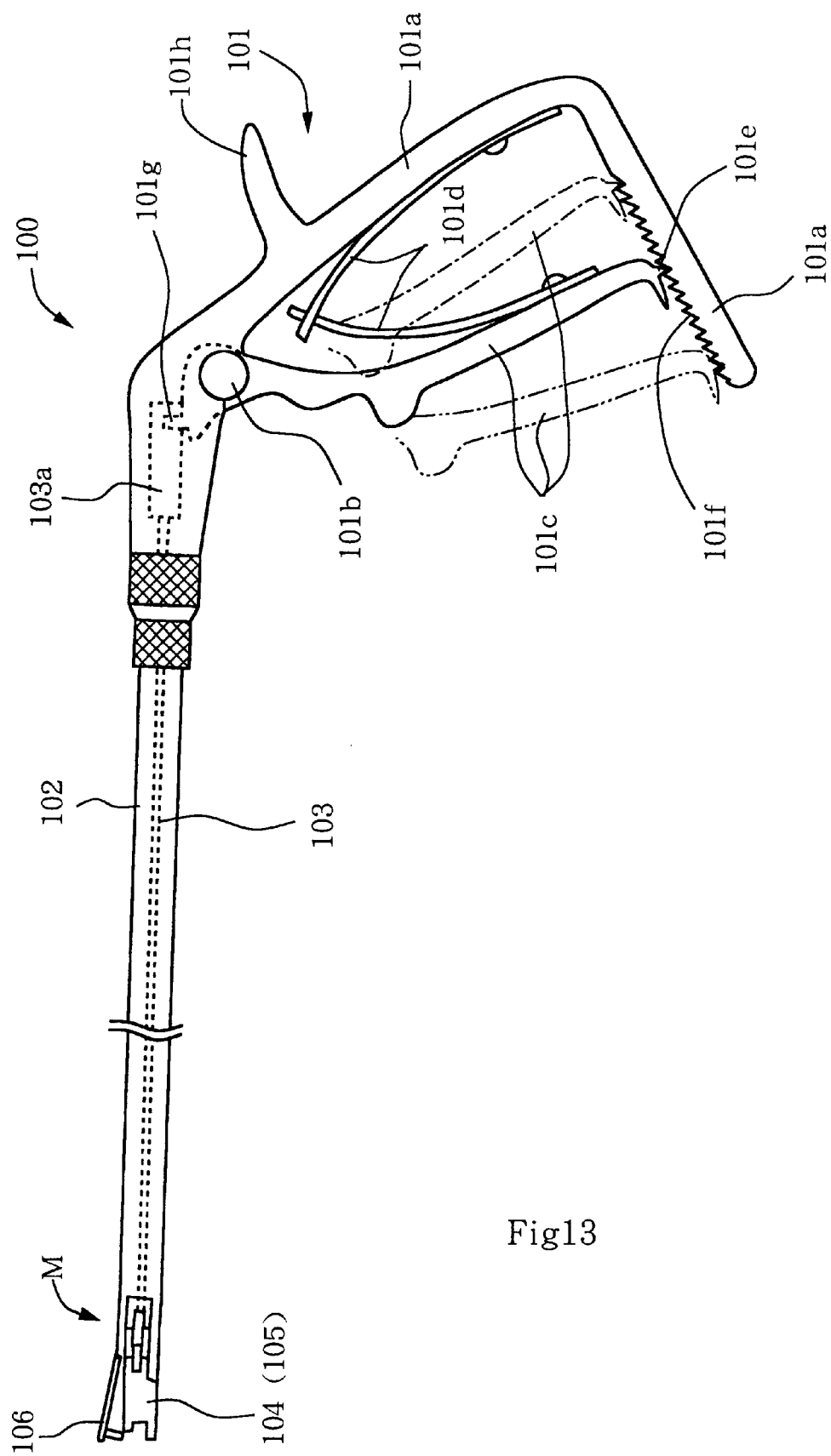
FIG. 13 is a schematic diagram showing an overall view of the suture ligating device in accordance with a fourth embodiment of the present invention.

As shown in FIG. 13, the suture ligating device 100 of this embodiment is generally formed in a gun shape and comprised of a manipulation portion 101, a hollow cylindrical body 102 (corresponding to the first rod member in the foregoing embodiments) integrally connected with the manipulation portion, an action rod member 103 (corresponding to the second rod member in the foregoing embodiments) movably inserted in the cylindrical body 102, a first top end member 104, a second top end member 105, a third top end member 106, and a link mechanism M which connects the above noted components. The ends of the first, second and third top end members are respectively formed, for example, in, a plate like shape.

The manipulation portion 101 is formed approximately in a U-shape and comprised of a frame 101*a* having a protrusion 101*h*, a manipulation lever 101*c* rotatably connected to the frame 101*a* via an axis 101*b*, and a spring means 101*d* for biasing the manipulation lever 101*c* in such a direction that the manipulation lever 101*c* is separated from the frame 101*a*. A protrusion 101*e* is provided at the bottom of the manipulation lever 101*c*. A number of saw tooth shaped grooves 101*f* are formed at the bottom of the frame 101*a*. Thus, by fitting the protrusion 101*e* in one of the grooves 101*f*, the manipulation lever 101*c* can be held in a desired position. The upper end of the manipulation lever 101*c* is inserted in a space provided inside the frame 101*a* and connected rotatably about the axis 101*b*. A projection 101*g* is formed at an upper end of the manipulation lever 101*c*, which engages with the action rod member 103.

The cylindrical body 102 is connected to the manipulation portion 101 by a fastener means such as a screw. The first top end member 104, the second top end member 105 and the third top end member 106 are provided at the top end of the cylindrical body 102 through the link mechanism M. As noted above, the action rod member 103 is inserted in the hollow portion of the cylindrical body 102. The action rod member 103 has a larger diameter portion 103*a* at an end in the manipulation portion 101. A hole is provided at the larger diameter portion 103*a* which engages with the projection 101*g* at the upper end of the manipulation lever 101*c*. Under this arrangement, according to the movement of the manipulation lever 101*c*, the action rod member 103 is moved, in proportion to the degree of the movement of the manipulation lever 101*c*, either backward or forward within the cylindrical body 102.

Figure 14:
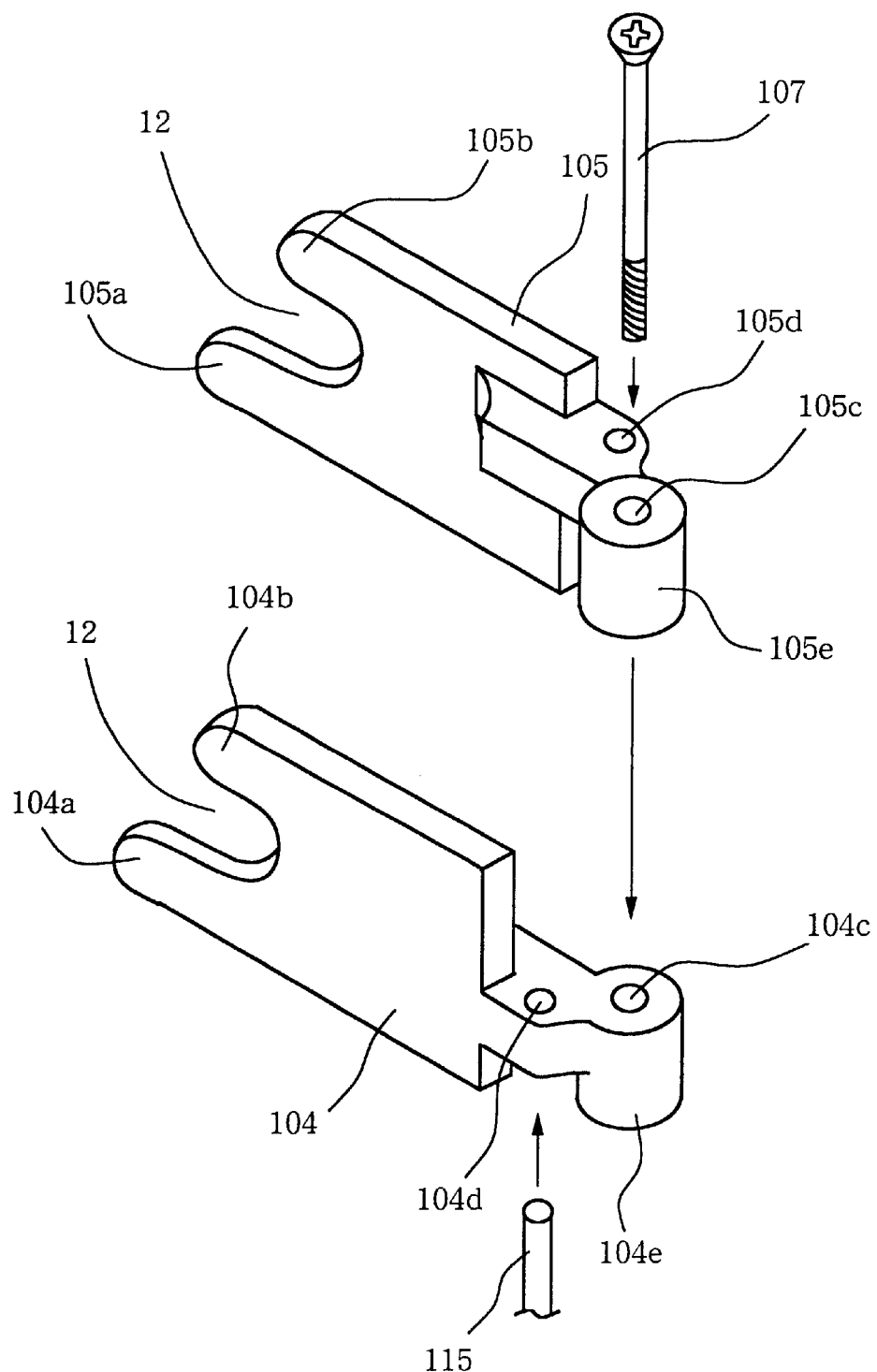
FIG. 14 is an expanded perspective view of the first and second top end members used in the fourth embodiment of the present invention of FIG. 13.

FIG. 14 is a perspective view of the first top end member 104 and the second top end member 105. The top end members 104 and 105 are provided with longer protrusions 104*a* and 105*a* and shorter protrusions 104*b* and 105*b* at the respective ends. As shown in FIG. 14, between the longer and shorter protrusions, a concave 12 is created at each of the first and second top end members 104 and 105. At a base of each of the first and second end members 104 and 105, two through holes 104*c*, 104*d* and 105*c*, 105*d* are provided in parallel. The first top end member 104 and the second top end member 105 are formed approximately in a symmetrical shape of a mirror image.

The first and second top end members 104 and 105 are juxtaposed with one another in a manner that the cylindrical body 105*e* is aligned on the cylindrical body 104*e*. Thus, the through hole 105*c* is positioned in the same axis on the through hole 104*c* through which a screw 107 is inserted as will be further described later. Accordingly, the first and second top end members 104 and 105 are rotatably attached in a symmetrical fashion. A pin 115 is inserted in the through holes 104*d* and 105*d*. Further explanation will be given later regarding the screw 107 and the pin 115.

Figure 15A:
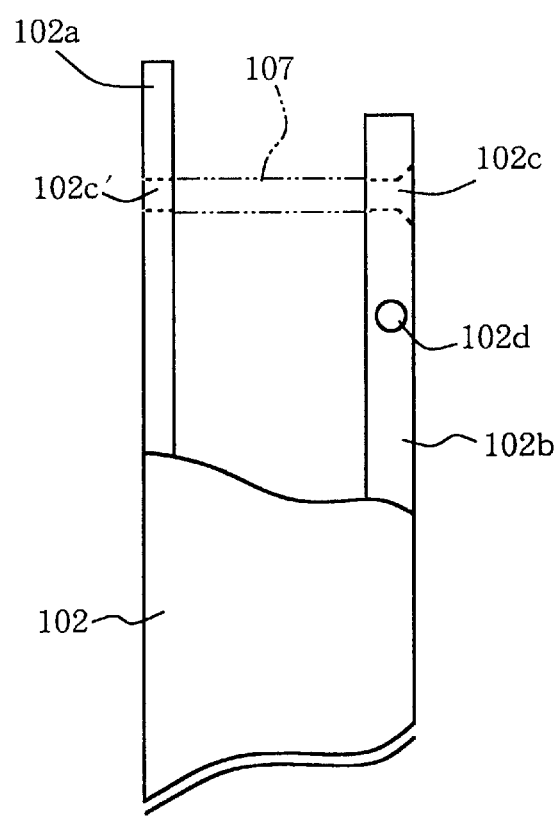
FIG. 15(a) is an expanded side view of the end portion of the cylindrical body in the fourth embodiment of the present invention shown in FIG. 13.
Figure 15B:
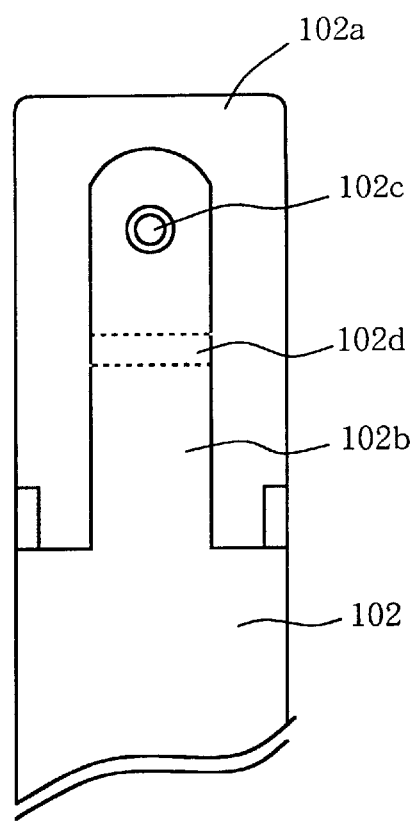
FIG. 15(b) is an expanded plan view of the end portion of the cylindrical body of the fourth embodiment of FIG. 13.

FIG. 15 shows an end portion of the cylindrical body 102. FIG. 15(*a*) is a side view of the end portion and FIG. 15(*b*) is a plan view thereof. At the end of the cylindrical body 102, two tongue pieces, namely a large tongue piece 102*a* and a small tongue piece 102*b*, are provided in parallel. A through hole 102*c* and a female thread hole 102*c'* are provided on an axis between the tongue pieces 102*a* and 102*b* as best shown in FIG. 15(*a*).

Further on the small tongue piece 102*b*, a through hole 102*d* is provided in a direction perpendicular to the direction of the through hole 102*c*. When aligning the through hole 104*c* and 105*c* of the first and second top end members 104 and 105, respectively, as described with reference to FIG. 14, the screw 107 is inserted in the through holes 102*c*, the through holes 105*c* and 104*c*, and fixed to the female thread hole 102*c'*. Consequently, the first and second top end members 104 and 105 are attached to the end of the cylindrical body 102 rotatably about the screw 107. The through hole 102*d* is to attach the third top end member 106 to the tongue piece 102*b*, which will be described in more detail below with reference to FIG. 16.

FIG. 16 shows the third top end member 106 wherein FIG. 16(*a*) is a side view thereof and FIG. 16(*b*) is a plan view thereof. In order that the relationship between each member can be easily understood, the cylindrical body 102 and the action rod member 103 are shown by imaginary lines. The third top end member 106 includes a drive body 106*b* which has a long and relatively thin figure extending in parallel with the cylindrical body 102. The third top end member 106 further includes a main body 106*a* which has a short and relatively thick figure and is approximately perpendicularly to the drive body 106b. At the end of the drive body 106b of the third top end member 106, a protrusion 106e is formed similar to the example of FIG. 11.

Figures 16A, 16B:
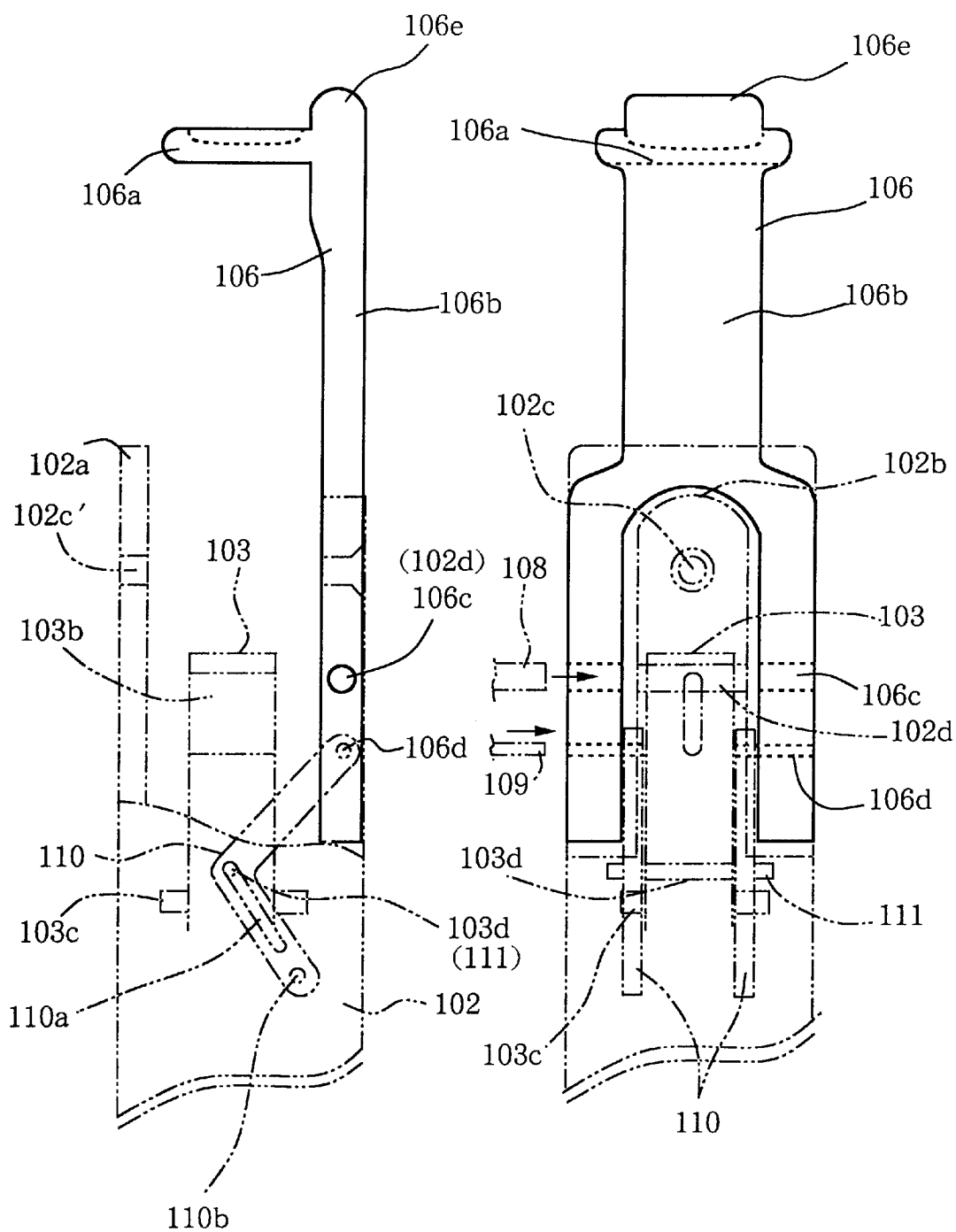
FIG. 16(a) is an expanded side view of third the top end member in the fourth embodiment of the present invention shown in FIG. 13.
FIG. 16(b) is an expanded plan view of the third top end member in the fourth embodiment of FIG. 13.

The lower end of the drive body 106b is forked into two as shown in FIG. 16(b) in such a way to cover the small tongue piece 102b of the cylindrical body 102. Through holes 106c and 106d are provided at the forked portion of the drive body 106b. The through hole 106c is aligned in the same axis of the through hole 102d of the small tongue piece 102b and connected each other by a pin 108 therein. A plate cam 110 having a shape of FIG. 16(a) is attached to the third top end member 106. This is achieved by a pin 109 which is inserted in holes 106d on the drive body 106b and a hole on an end of the plate cam 110. Thus, the plate cam 110 and the third top end member 106 is rotatably connected with one another. The other end of the plate cam 110 is rotatable connected to the cylindrical body 102 through a pin lob as shown in FIG. 16(a). The plate cam 110 has a dogleg shape. A guide groove 110a is formed in an inclined manner in which a pin 111 is inserted. The pin 111 is attached to the hole 103d of the action rod member 103. As noted above, the lower end of the plate cam 110 is rotatably connected to the cylindrical body 102 by the pin 110b.

Figures 17A, 17B:
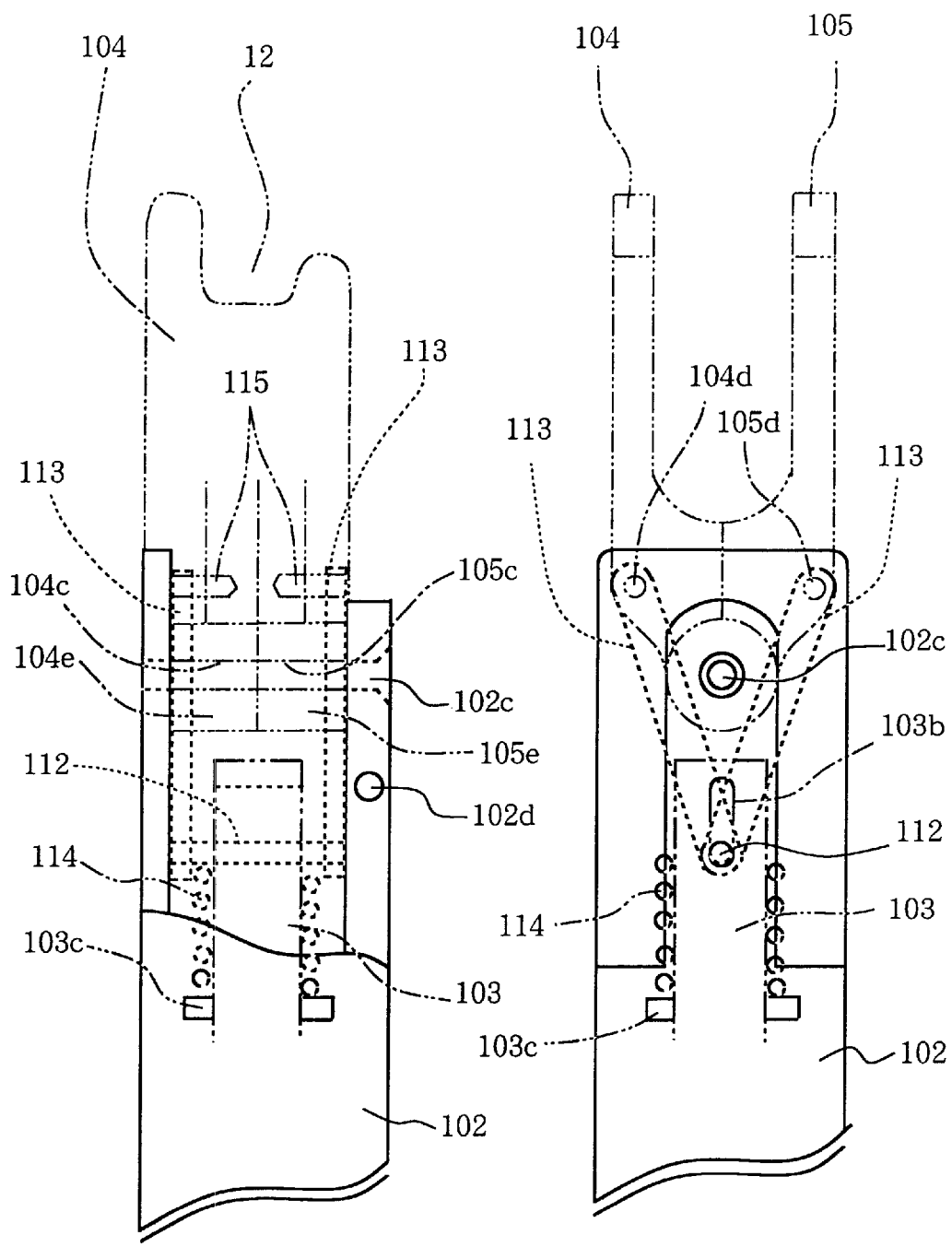
FIG. 17(a) is a side view of the fourth embodiment of FIG. 13 wherein the cylindrical body, rod member and first and second top end members are assembled.
FIG. 17(b) is a plan view corresponding to the side of FIG. 17(a).

FIG. 17(a) is a side view showing the cylindrical body 102 provided with the first and second top end members 104 and 105 and the action rod member 103, and FIG. 17(b) is a plan view corresponding to FIG. 17(a). As explained with reference to FIG. 14, the first and second top end members 104 and 105 are juxtaposed with each other, and the cylindrical portions 104e and 105e are aligned each other so that the through holes 104c and 105c are positioned in the same axis. The through hole 102c of the small tongue piece 102 is also aligned in the same axis of the through holes 104c and 105c. The screw 107 is then inserted into the through holes 102c, 104c and 105c and eventually fixed to the female thread 102c' of the larger tongue piece 102a.

In FIG. 17(b), a pin 112 is inserted in a slit 103b formed on the action rod member 103. The pin 112 is connected to each end of link plates 113 at both ends. Further in this arrangement, a coil spring 114 is provided between a flange portion 103c of the action rod member 103 and the pin 112 in a compressed condition. The other end of the link plate 113 is connected to the through holes 104d and 105d by the pin 115. As shown in FIG. 17(b), the pin 112 is positioned at about the bottom of the slit 103b even when pressed upward by the coil spring 114 because the first and second top end members 104 and 105 are pressingly closed with one another.

Under the foregoing configuration, if the action rod member 103 is retreated (moves in a downward direction of FIG. 17), the coil spring 114 is then extended corresponding to the degree of retreat of the action rod member 103. Relative to the cylindrical body 102, the pin 112 is moved inside the slit 103b upward in FIG. 17(b). Thus, the vertical position of the pin 112 remains unchanged until it reaches the top end of the slit 103b. When the pin 112 reaches the top end of the slit 103b and the action rod member 103 further moves downward, the pin 112 is then moved downward by being pressed by the top end of the slit 103b. Consequently, the link plates 113 are accordingly pulled downward, which makes the first and second top end members 104 and 105 begin to rotate around the screw 107 in the through hole 102c. Thus, the first and second top end members 104 and 105 are opened in proportion to the movement of the action rod member 103, which will be described again with reference to FIG. 20.

Figures 18A, 18B:
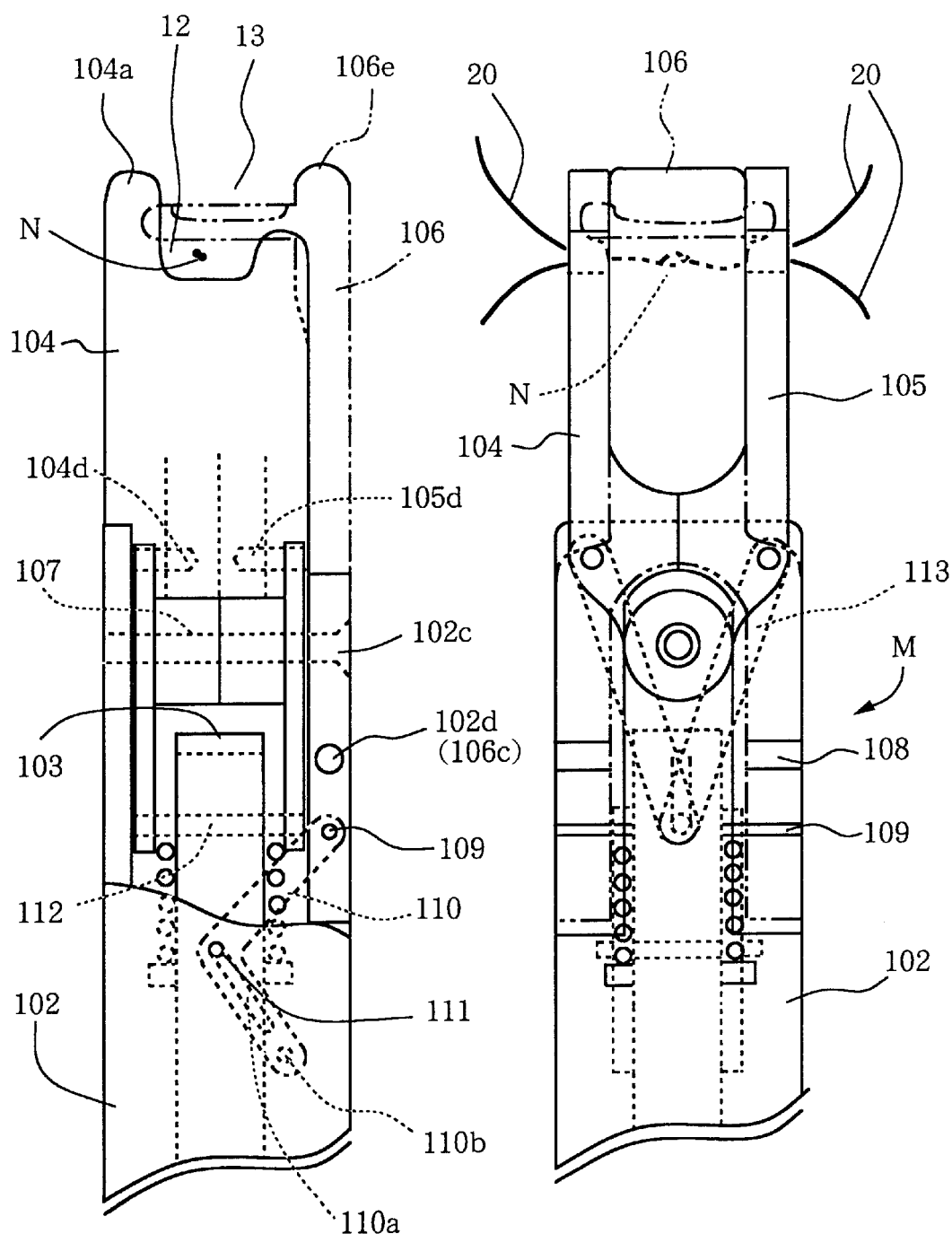
FIG. 18(a) is a side view of fourth embodiment of FIG. 13 wherein the third top end member is attached to the top end structure shown in FIG. 17.
FIG. 18(b) is a plan view of the assembly corresponding to the side view of FIG. 18(a).

FIGS. 18(a) and 18(b) are diagrams showing the overall assembly of the suture ligating device in the fourth embodiment of the present invention in which the third top end member 106 is illustrated by imaginary lines. FIG. 18(a) is a side view of the suture ligating device and FIG. 18(b) is a plan view thereof. FIGS. 18(a) and 19(b) also provide an overall view of the link mechanism M. In FIGS. 18(a) and 18(b), the first and second top end members 104 and 105 and the third top end member 106 are all closed. The action rod member 103 is in the position most advanced in the top end direction, i.e., the manipulation lever 101c is in the position nearest to the frame 101a as shown by the dotted line in FIG. 13.

Figure 19:
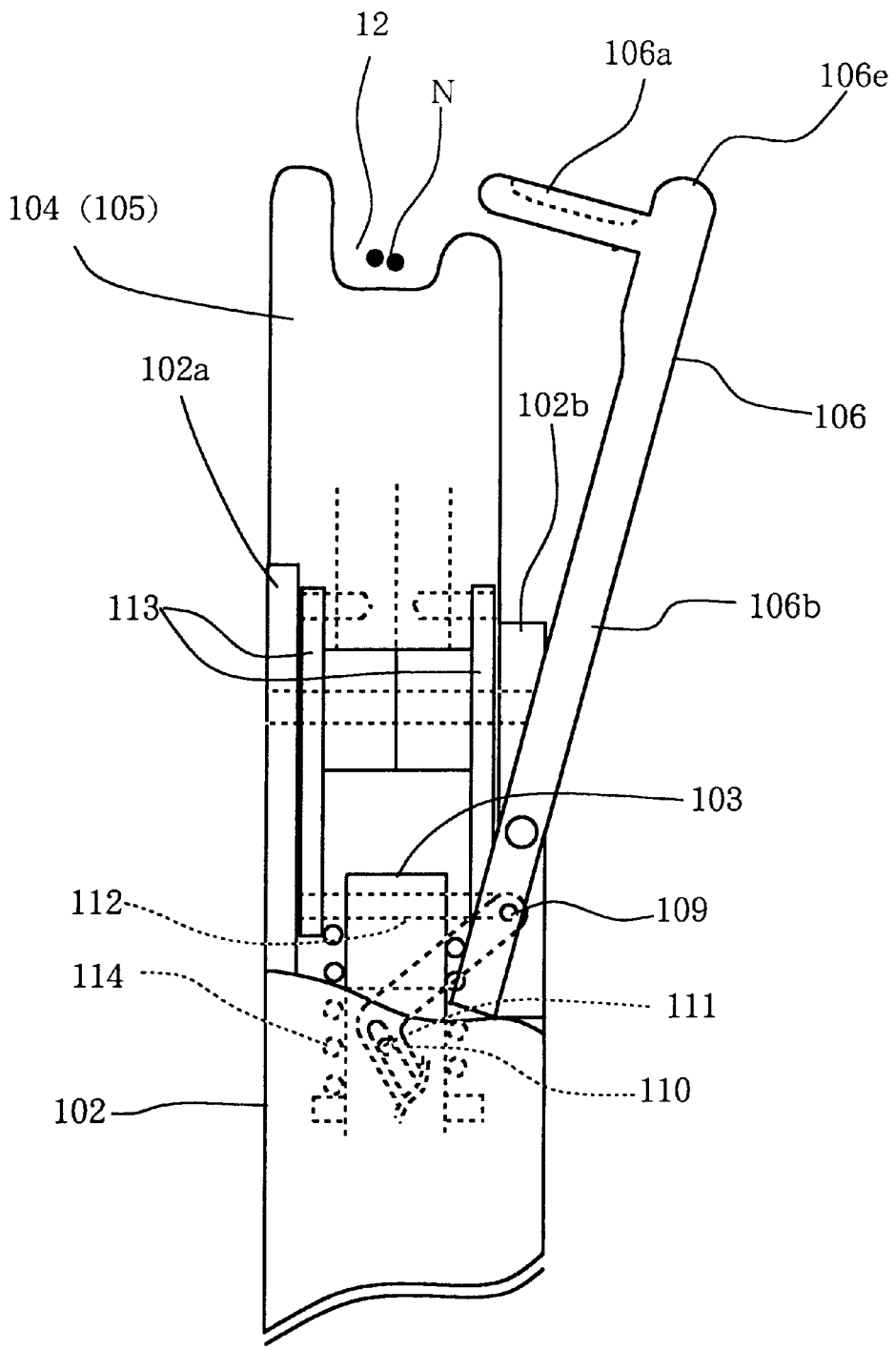
FIG. 19 is a side view of the assembly of FIG. 18 wherein only the third top end member is opened.

FIG. 19 shows the top end portion of the suture ligating device of the present invention wherein the manipulation lever 103c is retreated to the position shown by the solid line in FIG. 13, thereby moving the action rod member 103 backward in the cylindrical body 102, i.e., downward in FIG. 19. Because of the downward movement of the action rod member 103, the pin 111 in the inclined guide groove 110a of the plate cam 110 also moves downward along the groove, causing the pin 109 to move in a left direction of FIG. 19. Therefore, the third top end member 106 is opened in proportion to the downward movement of the action rod member 103.

During the first stage of the downward movement of the action rod member 103, the first and second top end members 104 and 105 are unchanged as noted above. This is because even if the action rod member 103 goes downward, the coil spring 114 is extended correspondingly so that the pin 112 maintains the same position as shown in FIG. 18. This situation continues until the pin 112 reaches the top end of the slit 103b.

Figure 20:
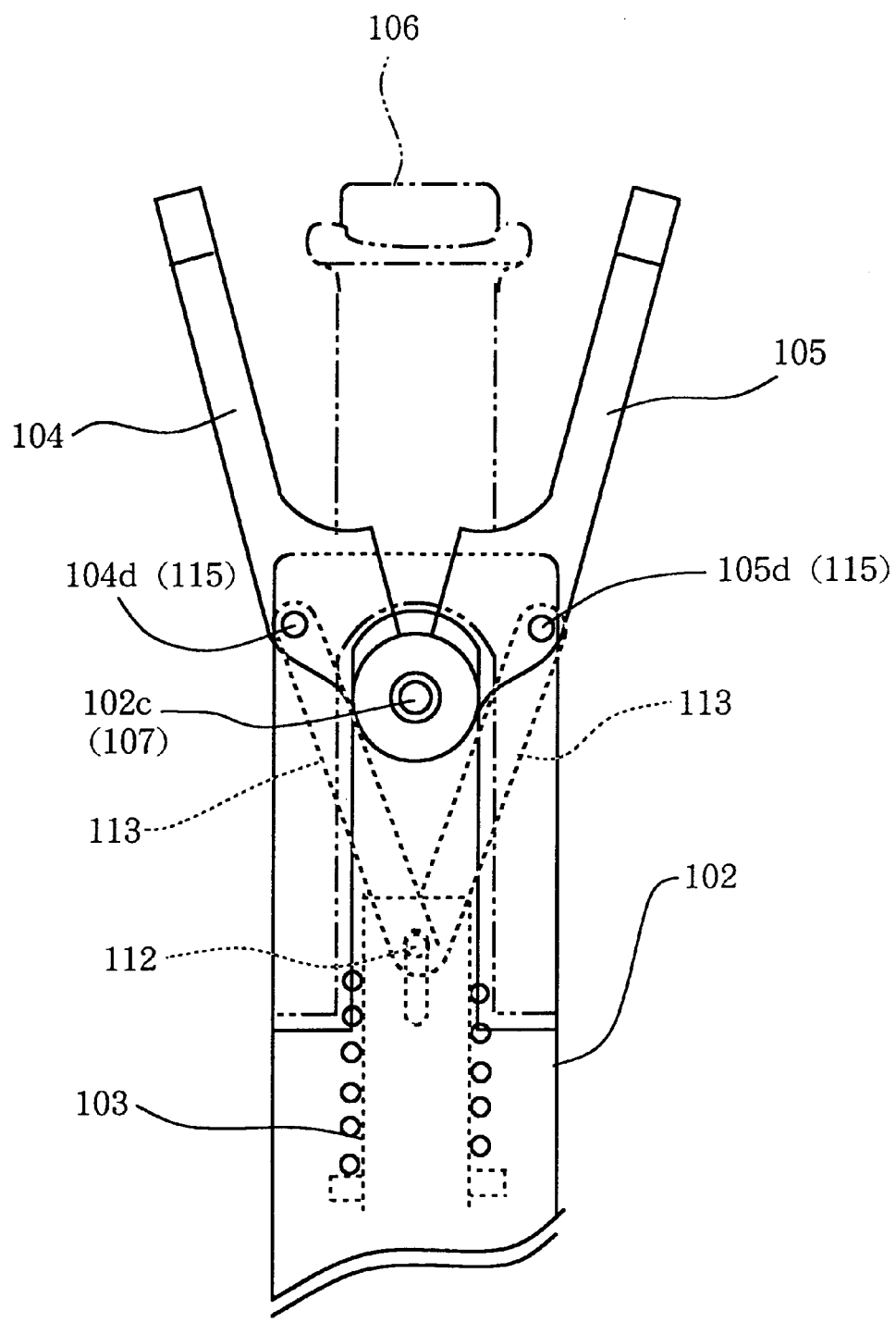
FIG. 20 is plan view of the assembly of FIG. 18 wherein the first, second and third top end members are all opened.

FIG. 20 shows the state of the suture ligating device wherein the action rod member 103 is further retreated and the manipulation lever 103c has reached the position shown by the two dotted line of FIG. 13. In this event, the first and second top end members 104 and 105 are opened in proportion to the movement of the action rod member 103. Thus, all of the three top end members are opened, which is achieved in the following.

Because the action rod member 103 moves backward (downward), the third top end member 106 withdrawn from the space formed by first and second top end members 104 and 105 as shown in FIG. 19. When the action rod member 103 further moves backward, the pin 112 is pressed downward by the top end of the slit 103b. Accordingly, the pin 112 is moved downward together with the action rod member 103, which pulls down the link plates 113 and thus the pins 115 of the first and second top end members 104 and 105. As a result, the first and second top end members 104 and 105 connected with these linkage means start to rotate around the screw 107 inserted into the through hole 102c. Consequently, the first and second top end members 104 and 105 are opened in right and left directions of FIG. 20, resulting in opening all of the top end members.

Next, the method of using the suture ligating device of FIGS. 13–20 is explained. First, as shown in FIG. 5, the tissues dissected by surgery are pierced by the suture 20. Then, the ends of the suture 20 are pulled back outside the human body and a knot N is formed as shown in FIG. 6.

In this stage, the suture ligating device is operated so that only the third top end member 106 is opened in a manner shown in FIG. 19. Then, the knot N is entered into the concaves 12 provided between the first and second top end members 104 and 105. Thereafter, the third top end member 106 is closed in a manner shown in FIG. 18. Since the knot N is placed in a closed space formed by the concaves 12 and the third top end member 106, the knot N can be transferred to the inner body of the patient without being lost or separated from the suture ligating device.

Figure 21:
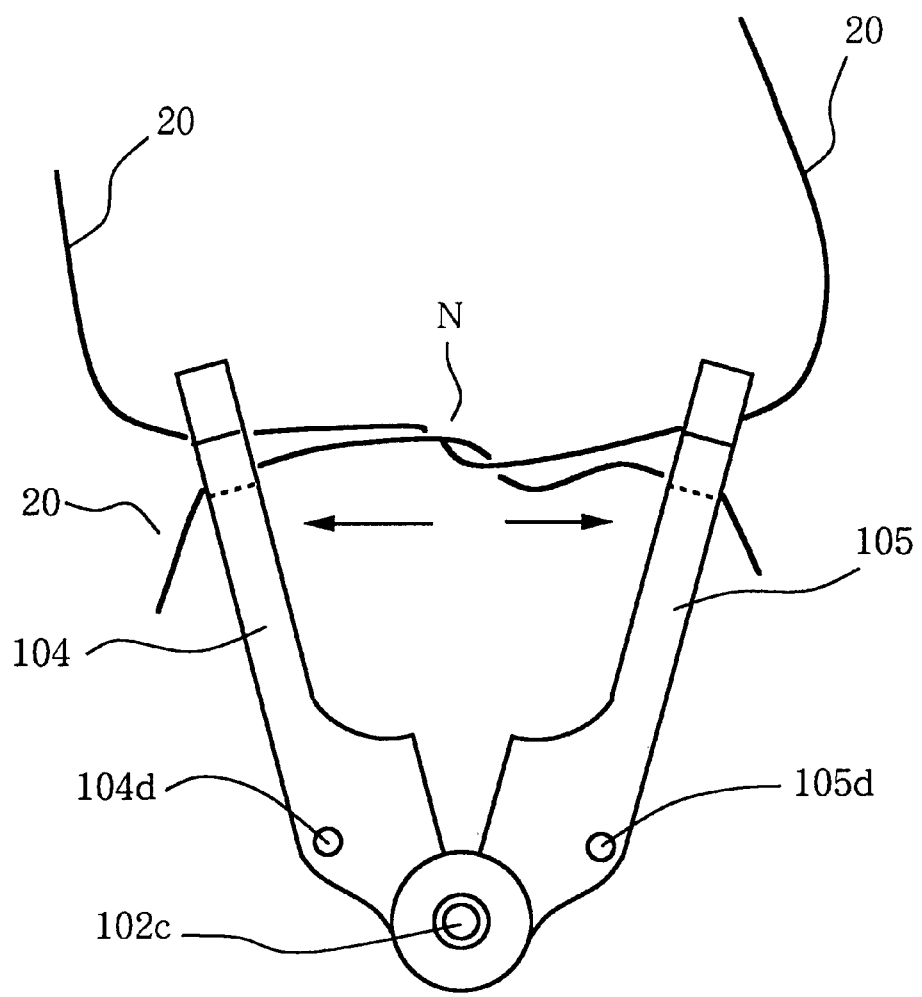
FIG. 21 is a schematic diagram showing a process of tying the knot under the condition of FIG. 20 where all the top end members are opened.

Under this condition, the suture ligating device is sent to the place where the tissues be ligated. After the top end of the suture ligating device has reached the place to be ligated, all of the three top end members are opened as shown in FIG. 20 and both ends of the suture 20 are pulled by a higher tension. By this operation, the tissues are tightly ligated therein. As shown in FIG. 21, since the knot forming suture 20 is pulled from right and left by the first and second top end members 104 and 105 which are opened and separated by a certain distance, the knot can be firmly ligated. This is because each end of the suture is pulled in the opposite direction, such as 180 degrees, from one another. Further, since the protrusions are prevented from contacting the tissues, the operation can be performed without damaging the tissues. By repeating the above noted procedure, a plurality of knots can be tied so that the suture will not become loose.

As shown in FIG. 18, the suture ligating device includes the protrusions 104a and 105a of the first and second top end members 104 and 105. The third top end member 106 is also provided with the projection 106e. As a result, a second concave 13 is formed at the top end of the third top end member 106. Therefore, it is also possible to form and transfer two knots at the same time by using this suture ligating device.

The size of the concaves 12 provided at the first and second top end members 104 and 105 may be varied depending on the kinds of the suture or thickness thereof. In this embodiment, the concaves are formed in a plate shape, although such a concave can be semicircular in cross section. Further, the top end face of the third top end member can be of any shape, such as a shape formed by cutting a hole in the axial direction or curvature in a segment shape as far as the top end face does not directly press the knot. For instance, the hole may not be a through hole, and the shape of the hole can be a complete circle, ellipse, parallelogram or trapezoid shape.

Although the manipulation portion is formed in a gun shape in this embodiment, it can be formed in other shapes such as an injector shape in which the action rod member 103 inside the cylindrical body can be manipulated. The manipulation portion can be made as an ordinary forceps type like the one shown in FIG. 1.

Although only preferred embodiments are specifically illustrated and described herein, it will be appreciated that many modifications and variations of the present invention are possible in light of the above teachings and within the purview of the appended claims without departing the spirit and intended scope of the invention.

What is claimed is:

1. A suture ligating device, comprising:
   a manipulation portion;
   first and second rod members for conducting a relative movement to each other in response to an operation of said manipulation portion;
   first and second top end members provided at an end of said first rod member, each of said first and second top end members having a U-shape and being parallel with each other; and
   a third top end member connected to the second rod member and rotatably moves relative to said first and second top end members for forming an open or closed space in accordance with the relative movement of the first and second rod members;
   wherein said U-shape of said first and second top end members forms two concaves opening in a top end direction, each of said two concaves is separated from each other by a predetermined distance, and the third top end member enters in a space having said predetermined distance between the first and second top end members or retreats from said space at a position ahead of a bottom of each of the concaves of the first and second top end members.

2. A suture ligating device as defined in claim 1, wherein said first and second rod members are configured in parallel to each other and said relative movement of the first and second rod members is performed in a longitudinal direction thereof.

3. A suture ligating device as defined in claim 1, wherein at the time when said third top end member enters in said space between the first and second top end members, both ends of said U-shape of each of the first and second top end members extend beyond an end of the third top end member, thereby forming a second concave by a combination of said first, second and third top end members.

4. A suture ligating device as defined in claim 1, wherein said third top end member is provided with a projection, and wherein said projection of said third top end member and at least one end of said U-shape of each of the first and second top end members extend beyond an end surface of said third top end member, thereby forming a second concave in combination of said first, second and third top end members.

5. A suture ligating device as defined in claim 1, wherein a top end face of said third top end member is formed in a groove like shape so that a knot of a suture positioned at said top end face is prevented from directly contacting with an overall surface of the top end face of the third top end member.

6. A suture ligating device as defined in claim 1, wherein a part of said first and second top end members are integrally connected to each other.

7. A suture ligating device as defined in claim 1, wherein said first and second top end members and said third top end member form a closed space when said third top end member enters in the space between said first and second top end members, and wherein a knot of a suture formed outside of a human body is secured in said closed space and transferred to tissues to be ligated inside of the human body.

8. A suture ligating device as defined in claim 1, wherein said first and second top end members and said third top end member form a closed space when said third top end member enters in the space formed between said first and second top end members, first and second knots of a suture are formed outside of a human body, and the first knot is placed on an end surface formed by said first, second and third top end members and the second knot is secured in said closed space, wherein the first and second knots are transferred to tissues to be ligated inside of the human body by inserting said suture ligating device in the human body while applying a pulling tension to the suture.

9. A suture ligating device, comprising:
   a manipulation portion;
   first and second slender members for conducting a relative movement to each other in response to an operation of said manipulation portion;
   first and second top end members provided at an end of said first slender member; and
   a third top end member connected to the second slender member and moves in a space provided between the first and second top end members in accordance with the relative movement of the first and second slender members;

wherein the first and second top end members are provided with concaves opening in a top end direction, the first and second top end members are separated to each other by a predetermined distance, the distance of which being variable in response to the relative movement of first and second slender members, and the third top end member enters in the space between the first and second top end members or retreats therefrom at a position ahead of a bottom of the concaves of the first and second top end members.

10. A suture ligating device as defined in claim 9, wherein the first and second top end members are provided with a link mechanism for changing the distance between the first and second top end members, said link mechanism being actuated by the relative movement of the first and second slender members, and a movement of said third top end member being conducted by said actuation.

11. A suture ligating device as defined in claim 9, wherein said first and second slender members are provided in parallel to each other and said relative movement of the first and second slender members is performed in a longitudinal direction thereof.

12. A suture ligating device as defined in claim 9, wherein at the time when said third top end member enters in the space between the first and second top end members, top ends of protrusions of the first and second top end members extending beyond an end of the third top end member, thereby forming a second concave by a combination of said first, second and third top end member.

13. A suture ligating device as defined in claim 9, wherein said third top end member is provided with a projection where said projection and protrusions of the first and second top end members extending beyond an end surface of said third top end member, thereby forming a second concave in combination with said first, second and third top end members.

14. A suture ligating device as defined in claim 9, wherein a top end face of said third top end member is formed in a concave shape so that a knot of a suture positioned at said top end face is prevented from directly contacting with the top end face of the third top end member.

15. A suture ligating device as defined in claim 9, wherein the third top end member is provided with a cam mechanism which causes an open and close movement of said third top end member in response to the relative movement of the first and second slender members, and the first and second top end members are provided with a link mechanism for changing the distance between the first and second top end members, said link mechanism being actuated when the relative movement of the first and second slender members exceeding beyond a predetermined degree.

16. A suture ligating device as defined in claim 9, wherein said first slender member has a cylindrical shape and said second slender member has a rod shape, said second slender member being provided within a cylindrical body of said second slender member and moving in forward and backward in said second slender member in response to said operation of said manipulation portion.

17. A suture ligating device as defined in claim 9, wherein said first and second top end members and said third top end member form a closed space when said third top end member enters in the space between said first and second top end members, and wherein a knot of a suture formed outside of a human body is secured in said closed space and transferred to tissues to be ligated inside of the human body.

18. A suture ligating device as defined in claim 9, wherein said first and second top end members and said third top end member form a closed space when said third top end member enters in the space formed between said first and second top end members, first and second knots of a suture are formed outside of a human body, and the first knot being placed on an end surface formed by said first, second and third top end members and the second knot being secured in said closed space, wherein the first and second knots are transferred to tissues to be ligated inside of the human body by inserting said suture ligating device in the human body while applying a pulling tension to the suture.

19. A suture ligating device as defined in claim 15, wherein said cam mechanism includes a guide groove inclined relative to the longitudinal direction of said first and second slender members in which a pin on said second slender member is inserted, thereby causing a movement transversal to said relative movement of the first and second slender members to control said open and close movement of said third top end member.

20. A suture ligating device as defined in claim 15, wherein said link mechanism includes a spring and a slit provided on said second slender member to maintain the same position of the first and second top end members until said relative movement of the first and second slender members exceeds said predetermined degree.

* * * * *